A61F 13/00
| | | |
|---|---|---|
| [19] | United States Patent | [11] Patent Number: 4,728,323 |
| | Matson | [45] Date of Patent: Mar. 1, 1988 |

[54] ANTIMICROBIAL WOUND DRESSINGS

[75] Inventor: Charles J. Matson, Stillwater, Minn.

[73] Assignee: Minnesota Mining and Manufacturing Company, St. Paul, Minn.

[21] Appl. No.: 889,671

[22] Filed: Jul. 24, 1986

[51] Int. Cl.$^4$ ............................................. A61F 13/00
[52] U.S. Cl. .................................... 604/304; 604/367; 128/156
[58] Field of Search ................... 604/896–897, 604/304–307, 367; 128/156, 132 D

[56] References Cited

U.S. PATENT DOCUMENTS

| | | | |
|---|---|---|---|
| 2,838,045 | 6/1958 | Ryznar | 128/156 |
| 2,934,066 | 4/1960 | Stowasser | 128/156 |
| 3,249,109 | 5/1966 | Maeth et al. | 128/156 |
| 3,800,792 | 4/1974 | McKnight et al. | 128/156 |
| 3,830,908 | 8/1974 | Klippel et al. | 424/28 |
| 3,903,882 | 9/1975 | August | 128/156 |
| 4,340,043 | 7/1982 | Seymour | 128/132 |
| 4,364,995 | 12/1982 | Crawford et al. | 428/336 |
| 4,387,156 | 6/1983 | Crawford et al. | 430/271 |
| 4,419,091 | 12/1983 | Behl et al. | 604/20 |
| 4,446,124 | 5/1984 | Fox et al. | 424/27 |
| 4,460,369 | 7/1984 | Seymour | 128/156 |
| 4,466,431 | 8/1984 | Tharrat et al. | 128/156 |
| 4,525,410 | 6/1985 | Hagiwara et al. | 604/367 |
| 4,541,426 | 9/1985 | Webster | 128/156 |
| 4,563,184 | 1/1986 | Korol | 128/156 |
| 4,588,400 | 5/1986 | Ring et al. | 128/156 |
| 4,643,179 | 2/1987 | Wang | 128/156 |

FOREIGN PATENT DOCUMENTS

| | | |
|---|---|---|
| 0099758 | 7/1983 | European Pat. Off. |
| 2092006 | 8/1982 | United Kingdom ............ 604/304 |
| 2134791A | 2/1984 | United Kingdom |

OTHER PUBLICATIONS

Maisel and Clang, *Handbook of Thin Film Technology*, pp. 1–68 (1970).
Holland, *Vacuum Deposition of Thin Films*, p. 464 (1961).
Kirk-Othmer, *Encyclopedia of Chemical Technology*, vol. 10, pp. 247–280, and vol. 14, pp. 691–693 and 264–265 (3rd Ed., John Wiley & Sons).
N. Grier, "Silver and Its Compounds," *Disinfection, Sterilization, and Preservation*, pp. 375–389 (Seymour Block, 3rd Ed., Lea & Febiger, Philadelphia, PA, 1983).
T. E. Wallis, *Textbook of Pharmacognosy*, pp. 298–299 (5th Ed., J. & A. Churchill Ltd., London, England, 1967).

*Primary Examiner*—C. Fred Rosenbaum
*Assistant Examiner*—Jerome R. Smith, Jr.
*Attorney, Agent, or Firm*—Donald M. Sell; James A. Smith; Dale E. Hulse

[57] ABSTRACT

Antimicrobial wound dressings are provided comprised of a substrate coated with an antimicrobially effective film of a silver salt. These antimicrobial wound dressings are prepared by vapor coating or sputter coating certain silver salts onto a variety of wound dressing substrates. Preferred silver salts are silver chloride and silver sulfate.

22 Claims, 5 Drawing Figures

ANTIMICROBIAL WOUND DRESSINGS

FIELD OF THE INVENTION

This invention relates to a wound dressing using a silver salt to impart antimicrobial activity to the dressing.

BACKGROUND OF THE INVENTION

Silver and silver compounds have long been known for their antimicrobial properties. See *Disinfection, Sterilization, and Preservation*, p. 375 (Seymour Block 3rd edition, Lea & Febiger, Philadelphia, 1983) (chapter 18 authored by N. Grier, entitled "Silver and Its Compounds").

Silver and silver compounds have been incorporated into a number of wound dressing articles. In particular, various wound dressing substrates have been coated with metallic silver. UK Patent Application GB No. 2 134 791 A describes a surgical dressing prepared by vapor coating or sputter coating Sphagnum moss with metallic silver or a silver/carbon composite. European Patent Application No. 0 099 758 describes a composite wound dressing comprising a semipermeable membrane, a permeable layer and a biodegradable layer wherein the permeable layer may be fabric coated, impregnated or plated with silver. U.S. Pat. No. 2,934,066 describes a metallized bandaging material prepared by vapor coating metallic silver onto a fiber fleece. U.S. Pat. No. 4,419,091 describes an electrode for ion therapy comprising a substrate of polymer fibers wherein each of the fibers is coated with silver.

Other means of providing silver or a silver salt at the site of wound have also been used in wound dressings. U.S. Pat. No. 4,340,043 describes an adhesive-coated liquid-impervious moisture-vapor permeable thin polymer sheet which has an antibacterial silver salt incorporated into the adhesive. U.S. Pat. No. 3,830,908 describes a synthetic plastic sheet powder-coated with an organic silver salt allantoin complexx. U.S. Pat. No. 3,800,792 describes a laminated collagen foam film dressing with finely divided metallic silver impregnated in the collagen layer. U.S. Pat. No. 4,446,124 describes a wound dressing comprising silver sulfadiazine incorporated in animal tissue, e.g. pigskin. Genetic Laboratories, Inc. is currently marketing a product called E-Z DERM TM temporary skin substitute for the treatment of burns. This product is a biosynthetic wound dressing having silver nitrate incorporated therein.

While the prior art described above has solved various problems encountered in the art of antimicrobial wound dressing, they do not possess the advantages of the wound dressings of this invention.

SUMMARY OF THE INVENTION

The present invention relates to an article useful as a wound dressing comprising a conformable substrate coated with an antimicrobially effective film of a silver salt. As used herein, an antimicrobially effective film is a film which exhibits a statistically significant improvement in the antimicrobial activity as compared with the corresponding control and as measured by the in vitro or in vivo tests described for the examples below. It has been found that a film coating of certain silver salts is more effective than a powder coating and that only certain silver salts yield an antimicrobially effective film.

The preferred embodiment is an adhesive-coated thin film dressing bearing a film of silver chloride or silver sulfate deposited on the adhesive-coated thin film dressing by vapor or sputter coating.

It has been found that the dressings of this invention having an antimicrobially effective film of a silver salt are more efficient, i.e., have greater antimicrobial activity while using less silver salt, than conventional wound dressings using silver salts.

This invention also relates to methods of preparing wound dressings are described above by vapor coating or sputter coating a substrate with an antimicrobially effective amount of a silver salt selected from the group consisting of silver bromide, silver fluoride, silver chloride, silver nitrate, silver sulfate, silver alkylcarboxylate, silver sulphadiazine or silver arylsulfonate.

DETAILED DESCRIPTION OF THE INVENTION

Figure 1:
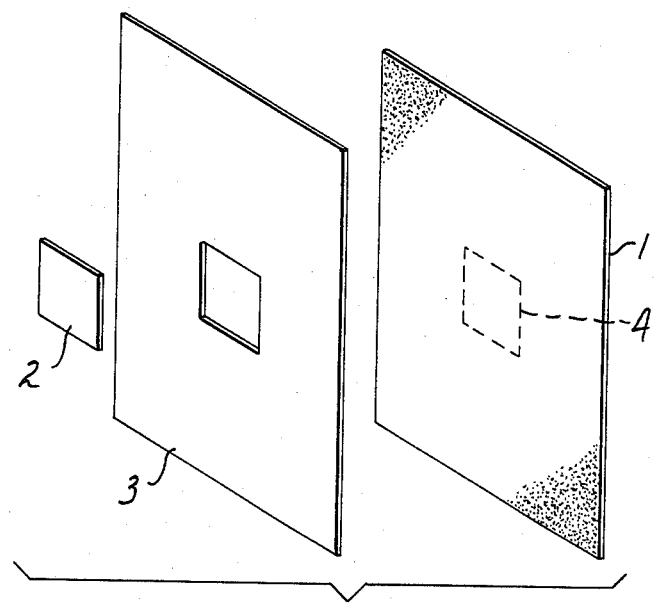
FIG. 1 shows an exploded view of a conventional wound dressing adapted to prepare an antimicrobial wound dressing of this invention.

To prepare a wound dressing of this invention, and antimicrobially effective film of silver salt is formed on the surface of a conformable substrate. The film of silver salt may be continuous or discontinuous so long as amounts of silver salts sufficient to have measurable antimicrobial activity are present. When the conformable substrate is fibrous, it is likely that the film is discontinuous with respect to the surface as a whole, but continuous with respect to portions of individual fibers.

The film is preferably deposited on the substrate by vapor or sputter coating techniques. In vapor coating, an amount of salt is vaporized and allowed to condense upon the surface of a substrate to form a film. In sputter coating, material is removed from a silver salt target, carried by a plasma, and deposited on the substrate to form a film. On a fibrous substrate, the film will generally coat at least a portion of individual fibers exposed on the surface of the substrate. While vapor or sputter coating of a pre-formed fibrous substrate is preferred, individual fibers can be coated with the film and then worked, e.g. blown, woven or knitted, into a fibrous substrate bearing an antimicrobially effective film.

The following are examples of suitable silver salts useful in the practice of the present invention: silver bromide, silver fluoride, silver chloride, silver nitrate, silver sulfate, silver alkylcarboxylate, silver sulphadiazine or silver arylsulfonate. Silver alkyl carboxylates are the silver salts of alkylcarboxylic acids preferably having from 1–12 aliphatic carbon atoms, more preferably 1–4 aliphatic carbon atoms, e.g. silver acetate. The aryl group of the arylsulfonate salts is an aromatic radical, e.g, optionally substituted phenyl or naphthyl, preferably alkaryl having 1 to 12 aliphatic carbon atoms, more preferably alkylphenyl having from 1 to 4 aliphatic carbon atoms, e.g., p-toluenesulfonate. Preferred salts are silver chloride and silver sulfate. It has been found that silver oxide and silver carbonate decompose when subjected to the energy necessary to vaporize or sputter. Silver iodide and silver sulfide can be deposited as films on a substrate by vapor or sputter coating, but such films have been found to be antimicrobially ineffective in that their films exhibited antimicrobial activity in vitro equivalent to the control having no film of a silver salt.

The substrate must be sufficiently conformable to conform to the contours of skin to which it will be applied as a wound dressing. The substrate is preferably a fabric or a polymeric film or foam having a tensile modulus of less than about 400,000 psi as measured by ASTM D-638 and D-882, preferably less than about 300,000 psi. The substrate may be chosen, for example, from the following: non-woven meshes such as Carelle® and Nylon 90® (both registered trademarks of Carolina Formed Fabrics Corporation), and N-Terface® (a registered trademark of Winfield Laboratories, Inc., Richardson, Tex.); woven meshes of fiberglass or acetate; gauze; polyurethane foams such as Hypol® (a registered trademark of W. R. Grace & Co., New York, NY); composite wound dressings such as Micropad® (a registered trademark of 3M Company, St. Paul, Minn.), and Biobrane® (a registered trademark of Woodroof Laboratories, Inc., Santa Ana, Calif.); and adhesive-coated, thin film dressings such as Tegaderm® (a registered trademark of 3M Company, St. Paul, Minn.), and OpSite® (a registered trademark of Smith and Nephew Inc., Columbia, SC). Currently preferred are adhesive-coated thin film dressings, polyurethane foam dressings and woven acetate meshes.

The substrate may be vapor coated using standard techniques. In particular, a convenient method of vapor coating is accomplished as follows. The substrate to be coated is covered with a mask in which the pattern to be vapor coated has been cut out. In the case of wound dressings with an adhesive coating and a release liner, the release liner may conveniently be used as the mask as shown in FIG. 1. FIG. 1 shows an exploded view of a conventional wound dressing available from 3M Co. under the tradename Tegaderm ™ brand surgical dressing that has been adapted for the manufacture of an antimicrobial wound dressing of this invention. The release liner is removed from the face of dressing 1 coated with adhesive. Weed 2 is removed, e.g. by stamping, from the liner to form mask 3. Mask 3 is then relaminated to dressing 1 leaving portion 4 of the adhesive-coated face of dressing 1 exposed. The dressing is then fastened to a concave metal support (not shown) sheet with a radius, e.g., 20 inch, of curvature. This metal support sheet with the attached dressing is suspended within an evacuable vessel, e.g., a bell jar, concave side down and at a suitable height, e.g., 20 inches, above a crucible. The material to be vaporized is placed in the crucible. The bell housing is lowered to its base and a vacuum, e.g., $10^{-4}$ to $10^{-7}$ Torr, is created to remove substantially all air and water molecules, which would interfere with the vapor coating process. The material is then vaporized by heating it to its melting point with an electron beam. The rate of vaporization can be controlled by the amount of energy applied to the crucible via the electron beam. A crystal monitor receives the same level of material deposition as the dressing and electronically relays the thickness of the layer being deposited. The concave nature of the support sheet to which the dressing is applied helps to assure that all dressings being vapor coated in a particular batch are receiving equivalent levels of deposition.

The coating may range broadly in thickness. A generally preferred range is from about 50 Angstroms to about 2,000 Angstroms depending on the silver salt which is being used. When the salt is silver chloride or silver sulfate, the preferred range is about 50 to about 500 Angstroms.

Wound dressings of the invention may also be prepared by sputter coating using standard techniques.

Figure 2:
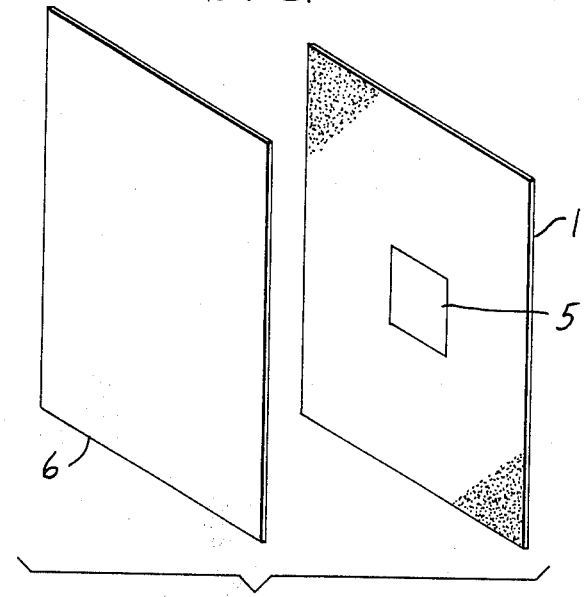
FIG. 2 shows an exploded view of wound dressing prepared from the adapted dressing of FIG. 1.

As shown in FIG. 2, dressing 1, as a result of the vapor coating procedure described above, bears square pattern 5 of an antimicrobial layer of a silver salt. A substitute release liner 6 can then be laminated to antimicrobial wound dressing 1 to protect the dressing prior to use.

The pattern of the silver salt deposition on the substrate may be varied by varying the pattern cut into the mask. The pattern may be a simple one, e.g., square pattern 5 as shown in FIG. 1, or it may be tailored for a specific wound application as shown in FIGS. 2-4.

Figure 3:
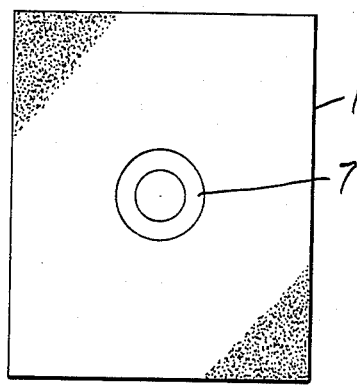
FIGS. 3–5 show plan views of various patterns of antimicrobially effective films of a silver salt on a substrate.

In FIG. 3, the film of silver salt forms ring 7 which can be centered over a percutaneous puncture site on the skin of a patient to antimicrobially protect such a wound.

Figure 4:
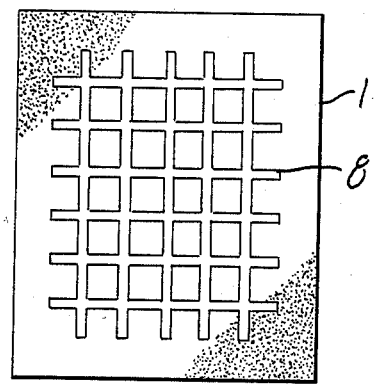

In FIG. 4, the film is in the form of a grid 8 which reduces the amount of silver salt needed to protect a large wound surface such as an abrasion.

Figure 5:
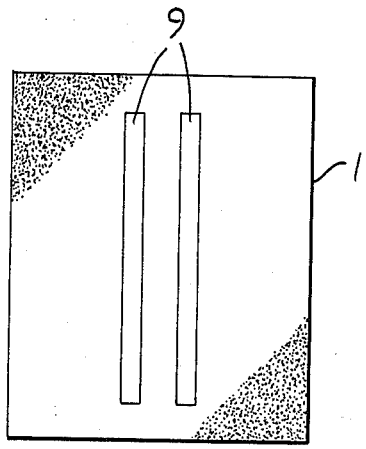

In FIG. 5, the film is in the form of parallel bars 9 which can be positioned on the skin of a patient with an incisional wound between the bars to antimicrobialy protect such a wound.

EXAMPLES

In Vitro Testing

The antimicrobial properties of the wound dressings of this invention are demonstrated in vitro using standard techniques as described below. Plexiglass chambers were constructed with two shelves each containing six circular wells (1.5 inch diameter by 0.25 inch deep). A one-eighth inch solid plexiglass sheet was fastened to the bottom side of each of the shelves. To prepare for use, the shelf with the wells was placed upside down, the dressing being tested was placed over the well, and finally the solid plexiglass sheet was placed on top of the dressings and fastened in place. When turned right side up, the dressings were sandwiched between and supported from underneath by this bottom plate. Each well was then filled with 3.0 ml of nutrient broth (available from Difco Laboratories). Inoculation of each well with the microbe being studied was then accomplished by adding a 0.1 ml (approximately $2 \times 10^3$ colony forming units) suspension of the microbes in sterile water. Incubation occurred for 24 hours at 37° C. in a humidified chamber. At the end of the incubation period the entire volume of each well was placed in a sterile test tube, vortexed, and serial one-hundred fold dilutions ($10^0$ to $10^{-6}$) were made for streaking onto sheep blood agar plates. Quantitative counts of colony forming units were made from these plates after 24 hours of incubation at 37° C. Standard microbial techniques were used in maintaining stock cultures of organisms as well as preparing inoculums. Special media were used when sheep blood agar plates were not appropriate, e.g. *Proteus vulgaris* was plated onto eosin methylene blue (5% agar) plates to prevent colony spreading.

In Vivo Testing

The antimicrobial properties of the wound dressings of the invention are demonstrated in vivo using standard techniques as described below. Female Yorkshire pigs (*Sus scrofa*) were given preanesthetic doses of atropine sulfate and ketamine. Surgical plane anesthesia was induced with a gaseous mixture of halothane, nitrous oxide, and oxygen through an endotracheal tube. The dorsal skin was then washed, shaved, and swabbed with several applications of Betadine ® (a registered trademark of the Purdue Frederick Company). The back of the pig was then covered with sterile surgical drapes leaving the Betadine ® covered skin exposed. The final application of Betadine ® was then repeatedly rinsed with sterile water to remove all traces of Betadine ®, thus resulting in a sterile surgical field. A 7.0 cm by 10.0 cm grid pattern was marked off on the skin to accommodate 16 dressings (6 cm by 7 cm). In the center of each grid, a 1 cm$^2$ wound was created using a keratome. These wounds were approximately 0.5 to 1.0 mm deep. Each wound was then inoculated with 10$\mu$ liter (approximately $2 \times 10^3$ colony forming units) of the culture being tested. Immediately after inoculation, the wound dressing being tested was placed over the wound site. Control wounds were covered with identical dressings which had not been coated with a silver salt. These inoculated wounds were left intact for 48 hours. Total surgical biopsy of the wounds occurred 48 hours post inoculation. This biopsy consisted of removing the exudate from underneath the wound by sterile syringe aspiration, swab removal of surface wound material, and surgical excision of the entire wound to a depth of approximately 3 mm. All samples from a single wound were placed in a sterile homogenizing tube, 3.0 ml of sterile phosphate buffered saline was added and then the samples were hand ground. One-hundred fold dilutions of this homogenate were then plated out on sheep blood agar plates. The plates were incubated for 24 hours then quantitatively analyzed for the number of colony forming units per wound.

It should be noted that moist healing conditions should be maintained in vivo to prevent the formation of a scab which can shield the bacteria of the colony from the antimicrobial film of a silver salt and thereby render the in vivo test inaccurate.

Vapor Coating Procedure

The articles described in the following examples were vapor coated in accordance with the procedure described above wherein the particulars set forth in the exemplary clauses (denoted by e.g.) were those actually employed to prepare the articles described below.

The following examples are provided to illustrate the invention, but are not intended to limit the invention.

EXAMPLES 1-8 AND COMPARATIVE EXAMPLES A-D

Tegaderm ® Brand Dressing Vapor Coated with Various Silver Salts

The adhesive-side release liner was removed from a sample of Tegaderm ® brand adhesive-coated, thin-film dressing and a 6.25 cm$^2$ square was cut out of the release liner. This liner was then reapplied and the sample was subjected to vapor coating as described with the desired silver compound. However, the silver oxide of Example A and the silver carbonate of Example B decomposed upon exposure to the electron beam used to vaporize the other silver salt samples. All samples were then tested for in vitro efficacy against *Staphylococcus aureus* as described above. The results are summarized in Table 1.

The efficacy ratings assigned in Table 1 are based on the following scale:

Efficacy Rating:
I = less than $10^3$ colony forming units/ml
II = $10^4$ to $10^5$ colony forming units/ml
III = $10^6$ to $10^7$ colony forming units/ml
IV = greater than or equal to $10^8$ colony forming units/ml which is equivalent to the control

TABLE 1

In vitro Efficacy of Vapor Coated Tegaderm ® Brand Dressing Against *Staphylococcus aureus*

| Example | Compound | Film Thickness (Å) | Efficacy Rating |
| --- | --- | --- | --- |
| 1 | Silver fluoride | 500 | II |
| 2 | Silver bromide | 500 | II |
| 3 | Silver chloride | 500 | I |
| 4 | Silver nitrate | 1100 | I |
| 5 | Silver sulfate | 100 | I |
| 6 | Silver acetate | 1000 | I |
| 7 | Silver sulphadiazine | <100 | III |
| 8 | Silver p-toluenesulfonate | <260 | II |
| A | Silver oxide | none | — |
| B | Silver carbonate | none | — |
| C | Silver iodide | 500 | IV |
| D | Silver sulfide | 1000 | IV |

EXAMPLES 9-20

In vitro Activity of Tegaderm ® Brand Dressing Vapor Coated with Silver Chloride Samples of Tegaderm ® brand dressings were vapor coated as described in Example 1 with silver chloride to give coatings of 50 Å, 125 Å, 250 Å, and 500 Å. These samples were tested in vitro against 8 different organisms. The results are shown in Table 2.

EXAMPLES 21-23

In vivo Activity of Tegaderm ® Brand Dressing Vapor Coated with Silver Chloride

Samples of Tegaderm ® brand dressings were vapor coated as described in Example 1 with silver chloride to give coatings of 500 Å, 1000 Å, and 2000 Å. These samples were tested for in vivo efficacy against *Staphylococcus aureus*. The results are shown in Table 3.

TABLE 3

In Vivo Study of the Efficacy of Tegaderm ® Brand Dressings Vapor Coated with Silver Chloride Against *Staphylococcus Aureus*

| Example | Film Thickness | Log of Colony Forming Units |
| --- | --- | --- |
| Control | — | 6.72 ± 0.59 |
| 21 | 500 Å | 3.27 ± 1.29** |
| 22 | 1000 Å | 2.95 ± 0.91** |
| 23 | 2000 Å | 3.75 ± 1.60* |

Inoculum per wound was $2 \times 10^3$ colony forming units
*Significant at 0.05 level in T-test
**Significant at 0.01 level in T-test

EXAMPLES 24 AND 25

In vitro Activity of Tegaderm ® Brand Dressings Vapor Coated with Silver Sulfate Samples of Tegaderm ® brand dressings were vapor coated as described in Example 1 with silver sulfate to give coatings of 50 Å and 230 Å. These samples were tested for in vitro efficacy against *Staphylococcus aureus*. The results are shown in Table 4.

TABLE 4

In Vitro Efficacy of Tegaderm ® Brand Dressings
Vapor Coated with Silver Sulfate Against
Staphylococcus Aureus

| Example | Film Thickness | Log of Colony Forming Units |
|---|---|---|
| Control | — | 9.16 ± 0.05 |
| 24 | 50 Å | 3.21 ± 1.44* |
| 25 | 230 Å | 2.97 ± 1.42* |

*Significant at 0.01 level in T-test

EXAMPLES 26–36

In vitro Activity of Various Substrates Vapor Coated with Silver Chloride

Silver chloride was vapor coated onto a variety of substrates. These substrates were then tested for in vitro efficacy against *Staphylococcus aureus*. Uncoated Tegaderm ® brand dressing was used as a control. The results are shown in Table 5.

TABLE 5

In vitro study of the Efficacy Against
*Staphylococcus Aureus* of Various Substrates Vapor
Coated with 500 Å of Silver Chloride

| Example | Substrate | Average Log of Colony Forming Units |
|---|---|---|
| Control* | Tegaderm ® | 9.60 |
| 26 | Tegaderm ® | 3.74 |
| 27 | Nylon mesh[1] | 2.95 |
| 28 | Non-woven mesh[2] | 3.51 |
| 29 | Non-woven mesh[3] | 2.73 |
| 30 | Fiberglass mesh[4] | 2.53 |
| 31 | Gauze[5] | 2.33 |
| 32 | Polyurethane foam[6] | 3.04 |
| 33 | Composite[7] | 4.17 |
| 34 | Composite[8] | 1.72 |
| 35 | Non-woven mesh[9] | 1.18 |
| 36 | Acetate mesh[10] | 1.70 |

*No silver chloride film
[1] Cerex ® - Nylon 6 from Monsanto Textiles Co., New York, NY
[2] Nylon 90 TM available from Carolina Formed Fabrics Corporation
[3] Carelle TM available from Carolina Formed Fabrics Corporation
[4] Orthopedic Products Division, 3M Company, St. Paul, MN
[5] Curity ® gauze sponges from the Kendal Company, Boston, MA
[6] Hypol TM foam available from W. R. Grace & Co., New York, NY
[7] Micropad TM available from 3M Company, St. Paul, MN
[8] Biobrane TM available from Woodruff Laboratories, Inc., Santa Ana, CA
[9] N—Terface TM available from Winfield Laboratories, Inc., Richardson, TX
[10] Available from Celanese Fibers Operation, Charlotte, NC.

EXAMPLES 37 AND 38

In vitro Activity of Tegaderm ® Brand Dressing Sputter Coated with Varying Amounts of Silver Chloride The in vitro activity of Tegaderm ® brand dressings sputter coated with silver chloride is shown in Table 6.

TABLE 6

In Vitro Efficacy Against *Staphylococcus aureus*
of Tegaderm ® Brand Dressing Sputter Coated
with Silver Chloride

| Example | Film Thickness | Average Log of Colony Forming Units |
|---|---|---|
| Control | — | 9.47 ± 0.11 |
| 37 | 500 Å | 4.59 ± 0.87* |

TABLE 6-continued

In Vitro Efficacy Against *Staphylococcus aureus*
of Tegaderm ® Brand Dressing Sputter Coated
with Silver Chloride

| Example | Film Thickness | Average Log of Colony Forming Units |
|---|---|---|
| 38 | 125 Å | 2.07 ± 2.75* |

*Significant at 0.01 level in T-test

EXAMPLES 39 AND 40 AND COMPARATIVE EXAMPLES E AND F

In vivo Activity of Vapor Coated or Powder Coated Silver Chloride Applied to Tegaderm ® Brand Dressing With or Without Adhesive Samples of Tegaderm ® brand dressing, with adhesive in Example 39 and without adhesive in Example 40, were vapor coated as described in Example 1 to give film coatings of 500 Å. Powdered silver chloride was powder-coated onto Tegaderm ® brand dressing with adhesive (Example E) and sodium chloride was vapor coated (Example F), as described in Example 1, onto Tegaderm ® brand dressing with adhesive to give a coating of 3200 Å. The results are shown in Table 7.

TABLE 7

In Vivo Activity of Vapor Coated or Powder Coated
Silver Chloride Applied to Tegaderm ® Brand Dressing
With and Without Adhesive

| Example | Form | Silver concentration ($\mu g/cm^2$) | Log of Colony Forming Units/ml |
|---|---|---|---|
| Control | — | — | 7.44 ± 1.12 |
| 39 | vapor coated onto adhesive | 21 | 2.77 ± 1.01 |
| 40 | vapor coated w/o adhesive | 21 | 5.46 ± 2.22 |
| E | powder coated onto adhesive | 120 | 5.88 ± 2.62 |
| F | vapor coated onto adhesive | —* | 8.03 ± 1.57 |

(Inoculum per wound = $1.2 \times 10^3$ cfu)
*434 $\mu g/cm^2$ of NaCl

The dressing of Example 40 was not significantly more effective than the Control Example because the absence of the adhesive layer raised the moisture vapor transmission of the dressing to a level sufficient to allow the wound to dry and form a hardened scab, which hardened scab shielded the bacteria from the silver chloride film. A backside coating, or a layer of adhesive as illustrated in Example 39, can be added to the dressing to lower the moisture vapor transmission of the dressing and to maintain a moist wound while healing.

Analysis of the X-ray diffraction pattern of a film of silver chloride deposited on a representative conformable substrate, i.e. Tegaderm ® brand dressing, by vapor coating revealed that the crystals of silver chloride were highly oriented, e.g, cubic axes perpendicular to the substrate and (200) and (400) planes parallel to the substrate, as compared with the relatively random orientation of the crystals of powdered silver chloride powder coated on an identical representative conformable substrate.

TABLE 2

In Vitro Efficacy of Tegaderm ® Vapor Coated with Silver Chloride

| Example | Film Thickness | Staphylococcus aureus | Pseudomonas aeruginosa | Escherichia coli | Proteus vulgaris | Staphylococcus epidermidis | Klebsiella pneumoniae | Candida albicans | Enterobacter cloacae |
|---|---|---|---|---|---|---|---|---|---|
| Control | — | 9.62 | 10.23 | 9.04 | 9.63 | 9.23 | 9.57 | 7.23 | 9.38 |
| Control | — | 9.45 | 10.49 | 9.15 | 9.59 | 8.69 | 9.38 | 7.11 | 9.39 |
| Control | — | 9.51 | 9.75 | 9.15 | 9.43 | 9.15 | 9.34 | 7.36 | 9.55 |
| 9 | 500 Å | 0.00 | 6.36 | 0.00 | 6.64 | 3.39 | 4.18 | 3.08 | 5.84 |
| 10 | | 0.00 | 6.28 | 0.00 | 7.18 | 3.32 | 1.00 | 3.11 | 5.97 |
| 11 | | 0.00 | 5.74 | 0.00 | 7.18 | 3.65 | 1.18 | 2.86 | 6.08 |
| 12 | 250 Å | 0.00 | 4.04 | 0.00 | 6.73 | 3.39 | 5.60 | 2.97 | 1.00 |
| 13 | | 0.00 | 3.60 | 0.00 | 7.00 | 4.06 | 1.00 | 3.11 | 4.61 |
| 14 | | 0.00 | 4.40 | 0.00 | 7.00 | 1.00 | 3.93 | 3.18 | 1.00 |
| 15 | 125 Å | 5.93 | 8.20 | 0.00 | 3.78 | 1.00 | 1.00 | 3.85 | 4.41 |
| 16 | | 1.00 | 7.36 | 0.00 | 4.59 | 0.69 | 4.75 | 3.95 | 4.51 |
| 17 | | 7.43 | 7.26 | 0.00 | — | 0.69 | 5.34 | 3.88 | 4.87 |
| 18 | 50 Å | 8.89 | 9.66 | 0.00 | 8.96 | 0.00 | 9.20 | 4.26 | 9.34 |
| 19 | | 9.11 | 9.91 | 0.00 | 8.43 | 0.00 | 9.34 | 3.54 | 9.38 |
| 20 | | 8.65 | 9.88 | 0.00 | — | 0.00 | 9.51 | 4.40 | 9.28 |

I claim:

1. An article useful as a wound dressing comprising a conformable substrate vapor coated with an antimicrobially effective film of silver chloride, said substrate having a low enough moisture vapor transmission to maintain a moist environment around the wound during healing so as to substantially prevent the formation of a hardened scab over the wound.

2. An article according to claim 1 wherein said film is from about 50 to about 2000 Angstroms in thickness.

3. An article according to claim 1 wherein the substrate is a fabric or a polymeric film or foam having a tensile modulus of less than about 400,000 psi.

4. An article according to claim 1 wherein the substrate is selected from the group consisting of an adhesive-coated, thin film sheet, a polyurethane foam, a woven mesh and a non-woven mesh.

5. An article according to claim 1 wherein a coating of pressure-sensitive adhesive is disposed between said substrate and said antimicrobially effective film.

6. An article useful as a wound dressing comprising a conformable substrate vapor coated with an antimicrobially effective film of a silver arylsulfonate, said substrate having a low enough moisture vapor transmission to maintain a moist environment around the wound during healing so as to substantially prevent the formation of a hardened scab over the wound.

7. An article in accordance with claim 6 wherein said arylsulfonate is optionally substituted phenyl or naphthyl sulfonate.

8. An article in accordance with claim 6 wherein said arylsulfonate is an alkarylsulfonate having 1 to 12 aliphatic carbon atoms.

9. An article in accordance with claim 6 wherein said arylsulfonate is phenyl or naphthyl sulfonate optionally substituted with alkyl groups having 1 to 4 carbon atoms.

10. An article in accordance with claim 6 wherein said silver arylsulfonate is silver toluenesulfonate.

11. An article in accordance with claim 10 wherein said silver toluenesulfonate is silver p-toluenesulfonate.

12. A method of preparing an antimicrobial wound dressing article comprising vapor coating a conformable substrate with an antimicrobially effective amount of a silver salt selected from the group consisting of silver fluoride, silver bromide, silver chloride, silver nitrate, silver sulfate, silver alkylcarboxylate, silver sulphadiazine, or silver arylsulfonate, said substrate having a low enough moisture vapor transmission to maintain a moist environment around the wound during healing so as to substantially prevent the formation of a hardened scab over the wound.

13. A metod of preparing an antimicrobial wound dressing article comprising sputter coating a conformable substrate with an antimicrobially effective amount of a silver salt selected from the group consisting of silver fluoride, silver bromide, silver chloride, silver nitrate, silver sulfate, silver alkylcarboxylate, silver sulphadiazine, or silver arylsulfonate, said substrate having a low enough moisture vapor transmission to maintain a moist environment around the wound during healing so as to substantially prevent the formation of a hardened scab over the wound.

14. An article useful as a wound dressing comprising a conformable substrate vapor coated with an antimicrobially effective film of silver sulfate, said substrate having a low enough moisture vapor transmission to maintain a moist environment around the wound during healing so as to substantially prevent the formation of a hardened scab over the wound.

15. An article useful as a wound dressing comprising a conformable substrate vapor coated with an antimicrobially effective film of a silver alkylcarboxylate, said substrate having a low enough moisture vapor transmission to maintain a moist environment around the wound during healing so as to substantially prevent the formation of a hardened scab over the wound.

16. An article in accordance with claim 15 wherein said silver alkylcarboxylate is silver acetate.

17. An article in accordance with claim 15 wherein said alkylcarboxylate has from 1 to 12 aliphatic carbon atoms.

18. An article in accordance with claim 15 wherein said alkylcarboxylate has from 1 to 4 aliphatic carbon atoms.

19. An article useful as a wound dressing comprising a conformable substrate vapor coated with an antimicrobially effective film of silver nitrate, said substrate having a low enough moisture vapor transmission to maintain a moist environment around the wound during healing so as to substantially prevent the formation of a hardened scab over the wound.

20. An article useful as a wound dressing comprising a conformable substrate vapor coated with an antimicrobially effective film of silver fluoride, said substrate having a low enough moisture vapor transmission to maintain a moist environment around the wound during healing so as to substantially prevent the formation of a hardened scab over the wound.

21. An article useful as a wound dressing comprising a conformable substrate vapor coated with an antimicrobially effective film of silver bromide, said substrate having a low enough moisture vapor transmission to maintain a moist environment around the wound during healing so as to substantially prevent the formation of a hardened scab over the wound.

22. An article useful as a wound dressing comprising a conformable substrate vapor coated with an antimicrobially effective film of silver sulphadiazine, said substrate having a low enough moisture vapor transmission to maintain a moist environment around the wound during healing so as to substantially prevent the formation of a hardened scab over the wound.

* * * * *

UNITED STATES PATENT AND TRADEMARK OFFICE
CERTIFICATE OF CORRECTION

PATENT NO. : 4,728,323

DATED : March 1, 1988

INVENTOR(S) : CHARLES J. MATSON

It is certified that error appears in the above-identified patent and that said Letters Patent is hereby corrected as shown below:

Column 1, line 41, "complexx" should read --complex--

Column 2, line 11, "are" should read --as--

Column 10, line 25, "metod" should read --method--

Signed and Sealed this

Twentieth Day of September, 1988

Attest:

DONALD J. QUIGG

*Attesting Officer*  *Commissioner of Patents and Trademarks*